United States Patent [19]

Shipchandler

[11] 4,314,080
[45] Feb. 2, 1982

[54] N-FORMYLATION OF 2-AMINO-2-METHYL-1-PROPANOL WITH CHLORAL HYDRATE

[75] Inventor: Mohammed T. Shipchandler, Libertyville, Ill.

[73] Assignee: International Minerals & Chemical Corp., Terre Haute, Ind.

[21] Appl. No.: 205,113

[22] Filed: Nov. 10, 1980

[51] Int. Cl.³ .............................................. C07C 102/00
[52] U.S. Cl. ................................................... 564/224
[58] Field of Search ....................................... 564/224

[56] References Cited

U.S. PATENT DOCUMENTS 3,636,036  1/1972  Ugi ...................................... 564/224

FOREIGN PATENT DOCUMENTS 2328527  3/1974  Fed. Rep. of Germany.
1379916  10/1961  France.

OTHER PUBLICATIONS

Poziomek, J. Org. Chem. 28, pp. 243-244.
Blicke et al., J. Am. Chem. Soc. 74 (1952), pp. 3933-3934.
Lambert et al., C. R. Acad. Sc. Paris 272 Series C (1971), pp. 2165-2168.

Primary Examiner—Arthur P. Demers
Attorney, Agent, or Firm—Robert H. Dewey

[57] ABSTRACT

A method for preparing 2-methyl-2-N-formylamino-1-propanol by the step of reacting 2-amino-2-methyl-1-propanol with chloral in about an equimolar ratio at ambient to elevated temperatures.

3 Claims, No Drawings

N-FORMYLATION OF 2-AMINO-2-METHYL-1-PROPANOL WITH CHLORAL HYDRATE

BACKGROUND OF THE INVENTION

This invention relates to a method for preparing 2-methyl-2-N-formylamino-1-propanol.

It is known from U.S. Pat. No. 3,636,036 to prepare N-formylamines, such as 2-methyl-2-N-formylamino-1-propanol (hereinafter referred to as N-formyl AMP), by reacting formic acid with an appropriate amine at the temperature of refluxing toluene. Compounds such as these are useful for the preparation of isocyanocarbonates which are useful as cross-linking and hardening agents. N-formyl AMP is also useful in the preparation of insecticidal compounds as disclosed in French Pat. No. 1,379,916.

N-formylamines in general can be prepared from the corresponding amine and chloral under anhydrous conditions (*J. Am. Chem. Soc.* 74, 3933 (1952)). Chloral has a pungent odor and requires special handling. Pozionek (*J. Org. Chem.* 28, 243 (1963)) reported the reaction of amines with chloral hydrate in water, thus avoiding the difficulties with chloral. This method, however, fails in the case of hindered amines, e.g. t-butylamine.

SUMMARY OF THE INVENTION

It is an object of this invention to provide a method for the preparation of N-formyl AMP.

Other objects of this invention will be apparent from the disclosure herein.

It is the discovery of this invention to provide a method for preparing N-formyl AMP by reacting 2-amino-2-methyl-1-propanol (AMP) with chloral.

DETAILED DISCUSSION

The method of the present invention was surprising and unexpected because it was known that the analogous amine, t-butylamine, did not react with chloral and AMP is much more hindered than is t-butylamine. However, it was discovered that AMP does in fact react readily with chloral, or preferably, chloral hydrate, at ambient temperatures. Chloral hydrate is preferred because it gives significantly higher yields.

According to the method of the present invention, AMP and chloral hydrate are reacted in about an equimolar amount in the presence of a solvent at ambient or somewhat elevated temperatures, e.g. up to 90° C. The formyl derivative can be readily isolated by evaporating the solvent. The product can be used as is or it can be recrystallized from a suitable solvent for higher purity if desired. Many suitable solvents are known and others can be easily determined. They include but are not limited to the lower aliphatic alcohols, e.g. from 1 to 6 carbon atoms, chlorinated hydrocarbons, e.g. chloroform, etc.

The invention will be better understood with reference to the following examples. It is understood, however, that the examples are intended only to illustrate the invention and it is not intended that the invention be limited thereby.

EXAMPLE 1

2-Amino-2-methyl-1-propanol (AMP) 8.9 g (0.1 mole) was dissolved in 50 ml of methanol and similarly chloral hydrate 16.5 g (0.1 mole) was also dissolved in 50 ml of methanol. The two solutions were mixed and allowed to sit overnight at room temperature. The methanol was then evaporated and the product formed on oil which solidified. Yield was 90%. It was recrystallized from a mixture of chloroform and cyclohexanol. The crystals were filtered and air dried, m.p. 57°–60° C. The nmr spectrum indicated that the product was 2-methyl-2-formylamino-1-propanol (N-formyl AMP).

EXAMPLE 2

The experiment of Example 1 was repeated in all essential details except that chloral 14.7 (0.1 mole) was substituted for chloral hydrate. The formyl derivative of AMP was obtained but in much poorer yield, 51%.

I claim:

1. A method for preparing 2-methyl-2-N-formylamino-1-propanol by the step of reacting 2-amino-2-methyl-1-propanol with chloral in about an equimolar ratio.

2. The method of claim 1 wherein the chloral is present as the hydrate.

3. The method of claim 1 wherein the reaction is conducted in the presence of a solvent.